United States Patent [19]

Shutske et al.

[11] Patent Number: 4,868,177

[45] Date of Patent: Sep. 19, 1989

[54] 1,2,3,4-TETRAHYDRO-1,9-ACRIDINEDIAMINES, PHARMACEUTICAL COMPOSITIONS AND USE

[75] Inventors: Gregory M. Shutske, Somerset; Kevin J. Kapples, Little York, both of N.J.

[73] Assignee: Hoechst-Roussel Pharmaceuticals, Inc., Somerville, N.J.

[21] Appl. No.: 269,038

[22] Filed: Nov. 29, 1988

[51] Int. Cl.[4] ............... A61K 31/44; A61K 31/54; C07D 219/10; C07D 417/02
[52] U.S. Cl. ............ 514/228.2; 514/232.8; 514/254; 514/290; 514/197; 544/60; 544/126; 544/361; 546/79; 546/93; 546/105
[58] Field of Search ............ 544/60, 126, 361; 546/93, 105, 79; 514/228.2, 232.8, 254, 290, 297

[56] References Cited

U.S. PATENT DOCUMENTS 4,695,573 4/1987 Shutske et al. ............ 546/79

Primary Examiner—Robert W. Ramsuer
Attorney, Agent, or Firm—Tatsuya Ikeda

[57] ABSTRACT

There are disclosed compounds having the formula

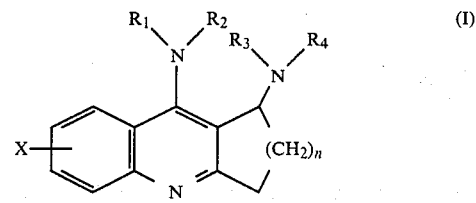

where
n is 1, 2 or 3;
X is hydrogen, loweralkyl, loweralkoxy, halogen, hydroxy, nitro or trifluoromethyl
$R_1$ and $R_2$ are each independently hydrogen, lower alkyl or arylloweralkyl, but both may not be arylloweralkyl simultaneously;
$R_3$ and $R_4$ are each independently hydrogen, lower alkyl, arylloweralkyl, formyl or lower alkylcarbonyl, or alternatively the group —$NR_3R_4$ taken as a whole constitutes

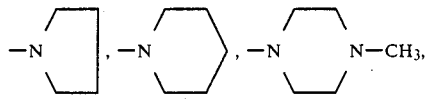

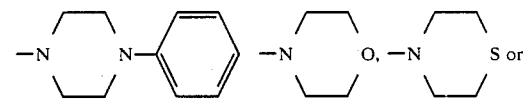

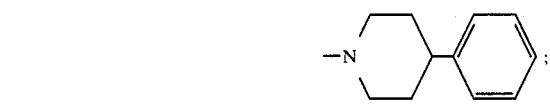

stereo isomers thereof and pharmaceutically acceptable acid addition salts thereof, which are useful for the treatment of various memory dysfunctions characterized by decreased cholinergic function, such as Alzheimer's disease.

26 Claims, No Drawings

1,2,3,4-TETRAHYDRO-1,9-ACRIDINEDIAMINES, PHARMACEUTICAL COMPOSITIONS AND USE

This invention relates to compounds having the formula

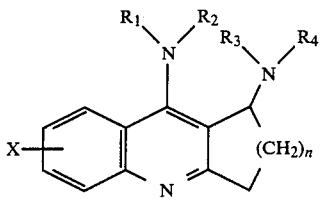

where
n is 1, 2 or 3;
X is hydrogen, loweralkyl, loweralkoxy, halogen, hydroxy, nitro or trifluoromethyl;
$R_1$ and $R_2$ are each independently hydrogen, loweralkyl or arylloweralkyl, but both may not be arylloweralkyl simultaneously;
$R_3$ and $R_4$ are each independently hydrogen, loweralkyl, arylloweralkyl, formyl or loweralkylcarbonyl, or alternatively the group —$NR_3R_4$ taken as a whole constitutes

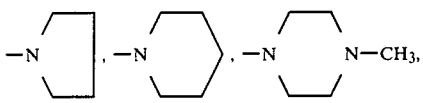

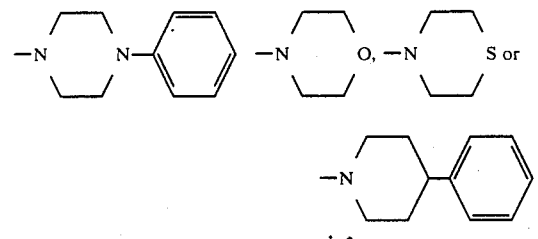

stereo isomers thereof and pharmaceutically acceptable acid addition salts thereof, which are useful for the treatment of various memory dysfunctions characterized by decreased cholinergic function, such as Alzheimer's disease.

Throughout the specification and the appended claims, a given chemical formula or name shall encompass all stereo, geometrical and optical isomers thereof where such isomers exist, as well as pharmaceutically aceeptable acid addition salts thereof and solvates thereof such as for instance hydrates.

The following definitions shall apply throught the specification and the appended claims.

Unless otherwise stated or indicated, the term loweralkyl denotes a straight or branched alkyl group having from 1 to 6 carbon atoms. Examples of said loweralkyl include methyl, ethyl, n-propyl, iso-butyl, pentyl and hexyl.

Unless otherwise stated or indicated, the term cycloalkyl denotes an alicyclic hydrocarbon group containing 3 to 7 carbon atoms. Examples of said cycloalkyl include cyclopropyl, cyclohexyl and cycloheptyl.

Unless otherwise stated or indicated, the term halogen shall mean fluorine, chlorine, bromine or iodine.

Unless otherwise stated or indicated, the term aryl shall mean an unsubstituted phenyl group or a phenyl group substituted with 1, 2 or 3 substituents each of which being independently loweralkyl, loweralkoxy, halogen, hydroxy or trifluoromethyl.

The compounds of this invention are prepared by utilizing one or more of the steps described below.

Throughout the description of the synthetic steps, the definitions of n, X, $R_1$ through $R_4$ are as given above unless otherwise stated or indicated.

STEP A:

A compound of Formula II is reacted with a diketone of Formula III to afford a compound of Formula IV. Typically, said reaction is conducted in a suitable solvent such as an etheral solvent including tetrahydrofuran, diethyl ether and dioxane at a temperature of about 30°–100° C.

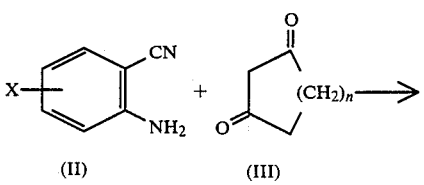

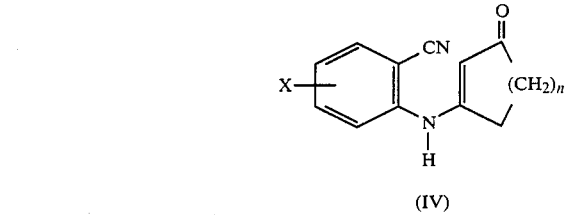

STEP B:

A compound of Formula V is prepared by cyclizing compound IV in the presence of a metallic halide such as cuprous chloride, cuprous bromide or cuprous iodide or the like used as a catalyst. Typically said cyclization reaction is conducted in a suitable solvent such as an ethereal solvent including tetrahydrofuran, diethyl ether and dioxane and in the presence of a catalyst and a basic inorganic salt such as potassium carbonate, potassium bicarbonate, sodium carbonate, sodium bicarbonate or the like, at a temperature of about 30°–100° C.

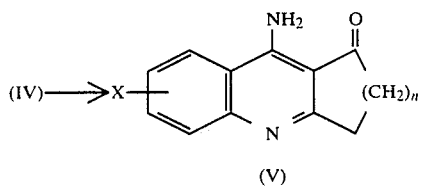

STEP C:

A compound of Formula VI (where X is not $NO_2$) is prepared by reacting compound V with a suitable metal hydride such as $LiAlH_4$ in a suitable solvent such as an ethereal solvent including tetrahydrofuran, diethyl ether, dioxane and mixtures thereof at a temperature of from about −20° to about 20° C., and thereafter hydrolyzing the product.

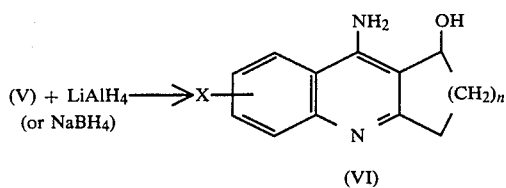

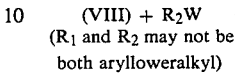

STEP D:

A compound of Formula VII is prepared by reacting compound VI with an amine of the Formula

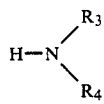

(where $R_3$ and $R_4$ are not formyl or loweralkylcarbonyl) in a suitable medium, for instance, an aromatic hydrocarbon such as toluene and preferably in the presence of a suitable catalyst such as p-toluenesulfonic acid. Typically the reaction is conducted at a temperature of 50° to 200° C.

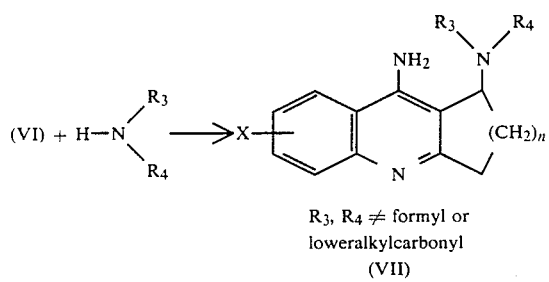

STEP E:

A compound of Formula VIII (where $R_1$ is not hydrogen and X is not OH) is prepared by reacting compound V with a compound of the formula $R_1W$, W being Cl, Br, I or $OSO_3CH_3$ (mesyloxy). Typically, said reaction is conducted in a biphasic system comprising a suitable organic solvent such as dichloromethane, chloroform, benzene, toluene or the like, a strongly alkaline aqueous phase such as 50% aqueous NaOH or the like, the starting compounds and a phase transfer catalyst such as tetrabutylammonium hydrogensulfate at a temperature of about 0°–50° C.

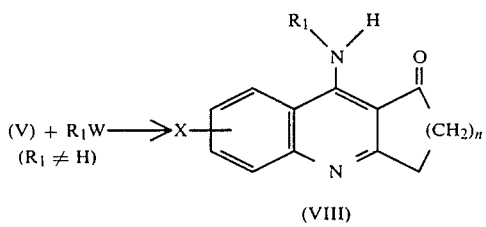

Where X is OH, the excluded compound can be prepared by subjecting a compound of Formula V where X is a loweralkoxy group (e.g. methoxy group) to a cleavage reaction conducted, for instance, with the aid of pyridine hydrochloride at a temperature of around 180° C.

STEP F:

In a manner similar to the one described above as STEP C, a compound of Formula IX (where $R_1$ and $R_2$ may not be both arylloweralkyl) is obtained by further reacting compound VIII with a compound of the formula $R_2W$, W being the same as defined above.

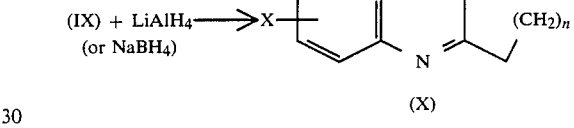

STEP G:

Compound IX obtained in STEP E or F is reduced with LiAlH$_4$ or NaBH$_4$ in substantially the same manner as in STEP C above to afford a compound of formula X.

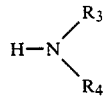

STEP H:

Compound X is reacted with an amine of the Formula (where $R_3$ and $R_4$ are not formyl or loweralkylcarbonyl) in substantially the same manner as in STEP D above to afford a compound of Formula IX.

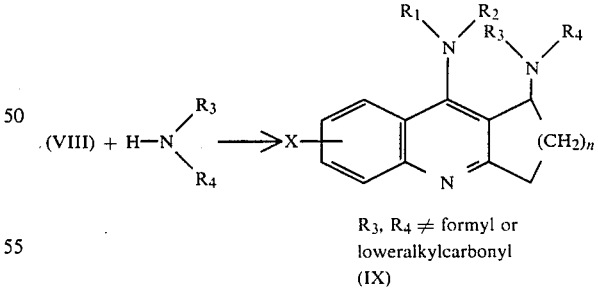

STEP I:

Compound VI is allowed to react with a mixture of diphenylphosphorylazide, triphenylphosphine and diethyl azodicarboxylate to afford an azide compound of Formula X.

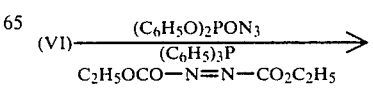

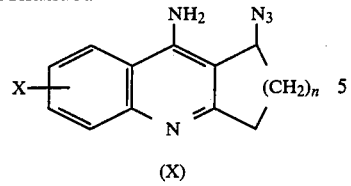

Typically, this reaction is conducted in a suitable solvent such as tetrahydrofuran at a temperature of 0° to 80° C.

STEP J:

Compound X is catalytically hydrogenated with a suitable catalyst such as palladium on carbon in a routine manner known to the art to afford a diamine compound of Formula XI.

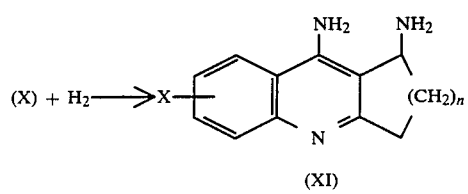

STEP K:

Compound XI is allowed to react with an acyl chloride of the formula $R_5COCl$ where $R_5$ is hydrogen or loweralkyl in a routine manner known to the art to afford a compound of Formula XII.

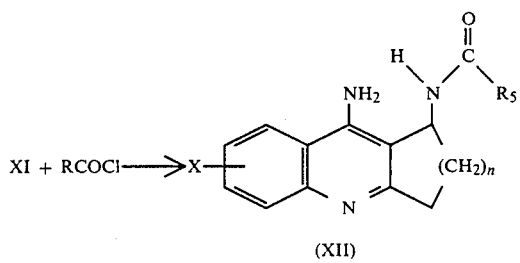

STEP L:

Compound XII is reduced with LiAlH$_4$ in a routine manner known to the art to afford a compound of Formula XIII.

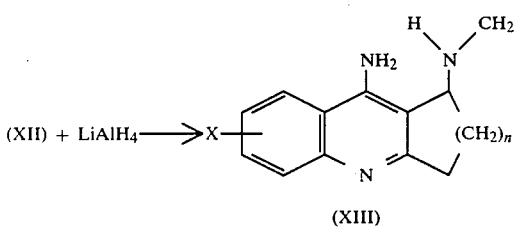

STEP M:

As a special case, a compound of Formula XIII where $R_5$ is methyl can be prepared in the following manner.

First, compound VI is allowed to react with acetonitrile in a suitable acidic medium, for instance, CF$_3$COOH containing a lower concentration of sulfuric acid to afford a compound of Formula XIV. Typically, this reaction is conducted at a temperature of 0° to 100° C.

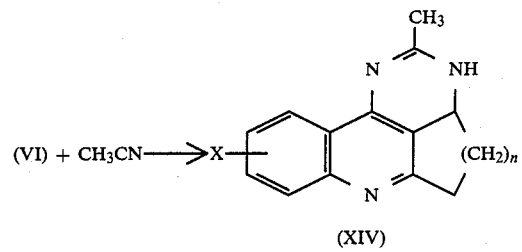

Secondly, compound XIV obtained above is allowed to react with LiAlH$_4$ in a suitable medium such as diethyl ether or tetrahydrofuran to afford a compound of Formula (XIIIa).

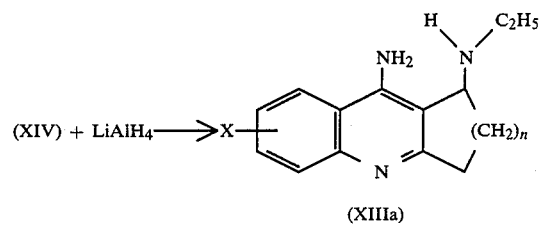

The compounds of Formula (I) of the present invention can be used for the treatment of various memory dysfunctions characterized by decreased cholinergic functions, such as Alzheimer's disease.

This utility can be ascertained by determining the ability of these compounds to inhibit the activity of the enzyme acetylcholinesterase and thereby increase the acetylcholine levels in the brain.

CHOLINESTERASE INHIBITION ASSAY

The ability to inhibit acetylchlinesterase was determined by the photometric method of Ellman et al., Biochem. Pharmacol. 7, 88 (1961). Results of some of the compounds of this invention are presented in Table 1 below along with those of some reference compounds.

TABLE 1

| Compound | Cholinesterase Inhibition IC$_{50}$ (molar conc.) |
|---|---|
| 1-(4-morpholinyl)-1,2,3,4-tetrahydro-9-acridinamine | $>1.0 \times 10^{-3}$ |
| 1-(1-piperidinyl)-1,2,3,4-tetrahydro-9-acridinamine | $8.4 \times 10^{-6}$ |
| 1-(1-pyrrolidinyl)-1,2,3,4-tetrahydro-9-acridinamine | $1.8 \times 10^{-5}$ |
| 1-(4-phenyl-1-piperazinyl)-1,2,3,4-tetrahydro-9-acridinamine, maleate | $>1.0 \times 10^{-3}$ |
| 1-(4-methyl-1-piperazinyl)-1,2,3,4-tetrahydro-9-acridinamine | $>1.0 \times 10^{-3}$ |
| N$_1$—butyl-1,2,3,4-tetrahydro-1,9-acridinediamine | $4.9 \times 10^{-5}$ |
| N$_1$—benzyl-1,2,3,4-tetrahydro-1,9-acridinediamine | $2.0 \times 10^{-5}$ |
| N$_1$—propyl-1,2,3,4-tetrahydro-1,9-acridinediamine | $1.3 \times 10^{-5}$ |
| N$_1$—(2-phenylethyl)-1,2,3,4-tetrahydro-1,9-acridinediamine | $1.9 \times 10^{-5}$ |
| N$_1$—ethyl-1,2,3,4-tetrahydro-1,9-acridinediamine, fumarate, hemi-hydrate | $4.8 \times 10^{-6}$ |
| N$_1$—(3,4-dimethoxybenzyl)-1,2,3,4-tetrahydro-1,9-acridinediamine | $3.9 \times 10^{-5}$ |
| 1-azido-1,2,3,4-tetrahydro-9-acridinamine, maleate | $1.2 \times 10^{-5}$ |
| (Reference Compounds) | |
| 9-Amino-1,2,3,4-tetrahydroacridine | $3.1 \times 10^{-7}$ |

TABLE 1-continued

| Compound | Cholinesterase Inhibition IC$_{50}$ (molar conc.) |
|---|---|
| Physostigmine | $6.0 \times 10^{-9}$ |

This utility can also be ascertained by determining the ability of these compounds to restore cholinergically deficient memory in the Dark Avoidance Assay. In this assay mice are tested for their ability to remember an unpleasant stimulus for a period of 24 hours. A mouse is placed in a chamber that contains a dark compartment; a strong incadescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment. Results of Dark Avoidance Assay for representative compounds of this invention and a reference compound are presented in Table 2.

TABLE 2

| | Dark Avoidance Assay | |
|---|---|---|
| Compound | Dose mg/kg body weight | % of animals with scopolamine induced memory deficit reversal |
| Physostigmine (Reference) | 0.31 | 20% |
| 1-(1-piperidinyl)-1,2,3,4-tetrahydro-9-acridinamine | 0.16 | 13% |
| N$_1$—propyl-1,2,3,4-tetrahydro-1,9-acridinediamine | 0.31 | 20% |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, whle effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablet, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

Examples of the compounds of this invention include
1-(1-pyrrolidinyl)-1,2,3,4-tetrahydro-9-acridinamine;
1-(1-piperidinyl)-1,2,3,4-tetrahydro-9-acridinamine;
1-(4-morpholinyl)-1,2,3,4-tetrahydro-9-acrdinamine; and
1-(4-phenyl-1-piperidinyl)-1,2,3,4-tetrahydro-9-acrdinamine;
N$_1$-propyl-1,2,3,4-tetrahydro-1,9-acridinediamine;
N$_1$-butyl-1,2,3,4-tetrahydro-1,9-acridinediamine;
N$_1$-benzyl-1,2,3,4-tetrahydro-1,9-acridinediamine;
N$_1$-(3,4-dimethoxybenzyl)-1,2,3,4-tetrahydro-1,9-acridinediamine;
N$_1$-(2-phenylethyl)-1,2,3,4-tetrahydro-1,9-acridinediamine;
1-(4-methyl-1-piperazinyl)-1,2,3,4-tetrahydro-9-acridinamine;
1-(4-phenyl-1-piperazinyl)-1,2,3,4-tetrahydro-9-acridinamine,;
N$_1$-hexanoxyl-1,2,3,4-tetrahydro-1,9-acridinediamine;
N$_1$-acetyl-1,2,3,4-tetrahydro-1,9-acridinediamine;
1-azido-1,2,3,4-tetrahydro-9-acridinamine;
1,2,3,4-tetrahydro-1,9-acridinediamine;
N$_1$-ethyl-1,2,3,4-tetrahydro-1,9-acridinediamine;

The following examples are presented in order to illustrate this invention.

EXAMPLE 1

1-(1-Pyrrolidinyl)-1,2,3,4-tetrahydro-9-acridinamine

9-Amino-1,2,3,4-tetrahydroacridin-1-ol (5.36 g) was refluxed overnight in 250 ml of toluene that contained pyrrolidine (7.10 g) and p-toluenesulfonic acid monohydrate (9.5 g). At the end of this time the reaction mixture was washed with an aqueous $K_2CO_3$ solution and then the organic phase was concentrated. The residue obtained in this manner was purified by flash chromatography (5% $Et_3N$, toluene) to give, after recrystallization from benzene/pentane, 2.91 g, m.p. 201°–203°.

ANALYSIS: Calculated for $C_{17}H_{21}N_3$: 76.37%C, 7.92%H, 15.72%N. Found: 76.13%C, 8.01%H, 15.33%N.

EXAMPLE 2

1-(1-Piperidinyl)-1,2,3,4-tetrahydro-9-acridinamine

9-Amino-1,2,3,4-tetrahydroacridin-1-ol (10.32 g) was refluxed in 500 ml of toluene containing 8.5 g of piperidine and 19.0 g of p-toluenesulfonic acid monohydrate. The reaction mixture was refluxed overnight and thereafter concentrated and triturated with aqueous $NH_3$. The crude product obtained in this manner was filtered off, triturated with $Et_2O$, and then recrystallized from benzene to give 7.02 g of analytically pure product, m.p. 215°–217° (d).

ANALYSIS: Calculated for $C_{18}H_{23}N_3$: 76.82%C, 8.24%H, 14.94%N. Found: 76.99%C, 8.20%H, 14.81%N.

EXAMPLE 3

1-(4-Morpholinyl)-1,2,3,4-tetrahydro-9-acridinamine

9-Amino-1,2,3,4-tetrahydroacridin-1-ol (15.0 g) was refluxed in 1000 ml of toluene that contained 12.18 g of morpholine and 9.285 g of benzaldehyde that had been freshly washed in $K_2CO_3$. The reaction mixture was refluxed overnight and allowed to cool. It was then filtered off and the crude product was purified by flash chromatography (20% PrOH/EtOAc) to give 2.20 g of analytically pure product after recrystallization from benzene/pentane, m.p. 215°–217°.

ANALYSIS: Calculated for $C_{17}H_{21}N_3O$: 72.05%C, 7.47%H, 14.83%N. Found: 71.92%C, 7.44%H, 14.70%N.

EXAMPLE 4

1-(4-Phenyl-1-piperidinyl)-1,2,3,4-tetrahydro-9-acridinamine

9-Amino-1,2,3,4-tetrahydroacridin-1-ol (5.36 g) was refluxed for 48 hours in 300 ml of toluene that contained 4-phenylpiperidine (8.06 g) and p-toluenesulfonic acid monohydrate (9.5 g). At the end of this time the reaction mixture was concentrated and the residue purified by flash chromatography (5% $Et_3N$/toluene) to give, after concentration of the product-containing fractions and recrystallization from EtOAc/pentane, 3.22 g of analytically pure product, m.p. 189°–190°.

ANALYSIS: Calculated for $C_{24}H_{27}N_3$: 80.63%C, 7.61%H, 11.75%N. Found: 80.79%C, 7.72%H, 11.72%N.

EXAMPLE 5

$N_1$-Propyl-1,2,3,4-tetrahydro-1,9-acridinediamine

A mixture of 9-amino-1,2,3,4-tetrahydroacridin-1-ol (8.66 g), p-toluensulfonic acid (8.5 g) and propylamine (19.9 ml) in 250 ml of toluene was refluxed with removal of water for twenty hours. An additional 4 ml of the amine was then added and reflux was continued for thirty hours.

The mixture was treated with a dilute NaOH solution and extracted with ethyl acetate (3x). The organics were then washed with water and dried (saturated NaCl solution, $MgSO_4$).

The desired amine was purified via flash chromatography (7.5% $Et_3N/C_6H_5CH_3$) to give 7.8 g of a yellow solid, m.p. 171°–177° C. A 3.85 g portion was recrystallized from methanol/water to give 2.79 g of yellow crystals, m.p. 175°–177° C.

ANALYSIS: Calculated for $C_{16}H_{21}N_3$: 75.26%C, 8.29%H, 16.45%N. Found: 75.40%C, 8.39%H, 16.52%N.

EXAMPLE 6

$N_1$-Butyl-1,2,3,4-tetrahydro-1,9-acridinediamine

A mixture of 9-amino-1,2,3,4-tetrahydroacridin-1-ol (8.26 g), n-butylamine (15.2 ml) and p-toluenesulfonic acid (8.8 g) in 250 ml of toluene was refluxed with removal of water for sixteen hours.

The mixture was then added to a dilute NaOH solution and extracted with ethyl acetate (3X). The combined organics were washed with water and dried ($MgSO_4$).

The amine was purified via flash chromatography (5% $Et_3N/C_6H_5CH_3$) to give 8.0 g of an off-white solid, m.p. 162°–166° C. A 3.9 g portion was recrystallized from methanol/water to give 3.41 g of a white powder, m.p. 164°–166° C.

ANALYSIS: Calculated for $C_{17}H_{23}N_3$: 75.80%C, 8.61%H, 15.60%N. Found: 75.86%C, 8.61%H, 15.64%N.

EXAMPLE 7

$N_1$-Benzyl-1,2,3,4-tetrahydro-1,9-acridinediamine

A mixture of 9-amino-1,2,3,4-tetrahydroacridin-1-ol (7.19 g), benzylamine (14.7 ml) and p-toluensulfonic acid (7.6 g) in 250 ml of xylenes were refluxed with removal of water for eighteen hours.

The reaction mixture was quenched into a dilute $K_2CO_3$ solution and extracted with ethyl acetate (2X). The organics were washed with water and dried (saturated NaCl, $MgSO_4$).

The amine was purified via flash chromatography (5% $Et_3N/C_6H_5CH_3$) to give 6.1 g of an off-white solid m.p. 161°–167° C. A 4.0 g portion was recrystallized from ethyl acetate/hexane to give 3.24 g of a white powder, m.p.: 166°–168° C.

ANALYSIS: Calculated for $C_{20}H_{21}N_3$: 79.17%C, 6.98%H, 13.85%N. Found: 79.15%C, 7.10%H, 13.75%N.

EXAMPLE 8

$N_1$-(3,4-Dimethoxybenzyl)-1,2,3,4-tetrahydro-1,9-acridinediamine

A mixture of 9-amino-1,2,3,4-tetrahydroacridin-1-ol (8.43 g), 3,4-dimethoxybenzylamine (11.9 ml) and p-toluenesulfonic acid (9.0 g) in 250 ml of toluene was refluxed with removal of water overnight.

The mixture was then added to iced NaOH solution and extracted with ethyl acetate (3x). The organics were washed with water and dried ($MgSO_4$).

The compound was purified via flash chromatography (2.5% Et₃N/EtOAc) to give 6.65 g of an off-white solid. After attempted purification via the fumaric acid addition salt, the free base was twice recrystallized from dichloromethane/hexane to give 2.65 g of a yellowish solid, m.p. 160°–162° C.

ANALYSIS: Calculated for $C_{22}H_{25}N_3O_2$: 72.70%C, 6.93%H, 11.56%N. Found: 72.66%C, 6.88%H, 11.54%N.

EXAMPLE 9

$N_1$-(2-Phenylethyl)-1,2,3,4-tetrahydro-1,9-acridinediamine

A mixture of 9-amino-1,2,3,4-tetrahydroacridin-1-ol (8.82 g), phenylethylamine (15.6 ml) and p-toluensulfonic acid (8.7 g) in 250 ml of toluene was refluxed with removal of water for twenty hours. The mixture was then treated with a dilute NaOH solution, and extracted with ethyl acetate (3x). The combined organics were washed with water and dried (saturated NaCl solution, MgSO₄).

The amine was purified via flash chromatography (7.5% Et₃N/C₆H₅CH₃) to give 10.6 g (81%) of a yellowish solid, m.p. 124°–128° C. A 4.02 g portion was recrystallized from ethyl acetate/hexane to give 3.05 g (61%) of a white powder, m.p. 120°–122° C.

ANALYSIS: Calculated for $C_{21}H_{23}N_3$: 79.46%C, 7.30%H, 13.24%N. Found: 79.63%C, 7.26%H, 13.37%N.

EXAMPLE 10

1-(4-Methyl-1-piperazinyl)-1,2,3,4-tetrahydro-9-acridinamine

9-Amino-1,2,3,4-tetrahydroacridin-1-ol (5.36 g) was refluxed for 48 h in 300 ml of toluene that contained 1-methylpiperazine (5.06 g) and p-toluenesulfonic acid monohydrate (9.5 g). At the end of this time the reaction mixture was distributed between EtOAc and aqueous K₂CO₃ and then the combined organic phase was concentrated and the residue purified by flash chromatography (5% Et₃N/EtOAc) to give, after concentration of the product-containing fractions and recrystallization from EtOAc, 2.30 g of analytically pure product, m.p. 200°–202°.

ANALYSIS: Calculated for $C_{18}H_{24}N_4$: 72.94%C, 8.16%H, 18.90%N. Found: 72.92%C, 8.27%H, 18.80%N.

EXAMPLE 11

1-(4-Phenyl-1-piperazinyl)-1,2,3,4-tetrahydro-9-acridinamine, maleate

9-Amino-1,2,3,4-tetrahydroacridin-1-ol (5.36 g) was refluxed for 24 h in 300 ml of toluene that contained 1-phenylpiperazine (8.10 g) and p-toluensulfonic acid monohydrate (9.5 g). At the end of this time the reaction mixture was distributed between EtOAc and aqueous K₂CO₃ and then the combined organic phase was concentrated and the residue purified by flash chromatography (5% Et₃N/toluene) to give, after concentration of the product-containing fractions and recrystallization from CH₂Cl₂-pentane, a product that contained a high mass weight impurity by mass spectrometry. The maleate was formed in isopropanol, filtered off and recrystallized from MeOH/Et₂O to give 3.03 g of analytically pure product, m.p. 205°–207°.

ANALYSIS: Calculated for $C_{23}H_{26}N_4C_4H_4O_4$: 68.34%C, 6.37%H, 11.81%N. Found: 68.25%C, 6.36%H, 11.71%N.

EXAMPLE 12

$N_1$-Hexanoyl-1,2,3,4-tetrahydro-1,9-acridinediamine

To a chilled solution of 1,2,3,4-tetrahydro-1,9-acridinediamine (4.96 g) and triethylamine (3.6 ml) in 100 ml of tetrahydrofuran was added hexanoyl chloride (3.6 ml). This was stirred for five minutes, then quenched into a dilute NaOH solution. The aqueous phase was extracted with ethyl acetate (3x) and dried (MgSO₄). The organics were concentrated to a semi-solid which was triturated with ethyl ether to give 3.32 g of a pale yellow powder, m.p. 205°–211° C. (dec.). This was recrystallized from methanol/water to give 2.54 g of a pale yellow powder, m.p. 214°–217° (dec.).

ANALYSIS: Calculated for $C_{19}H_{25}N_3O$: 73.28%C, 8.09%H, 13.49%N. Found: 73.02%C, 7.94%H, 13.33%N.

EXAMPLE 13

$N_1$-Acetyl-1,2,3,4-tetrahydro-1,9-acridinediamine, hemi-fumarate, hydrate

To a chilled mixture of 1,2,3,4-tetrahydro-1,9-acridinediamine (3.3 g) and triethylamine (2.4 ml) in 100 ml of tetrahydrofuran was added a solution of acetyl chloride (1.2 ml) in 5 ml of THF. This was stirred for 1.5 hours, then quenched into dilute NaOH solution and extracted with ethyl acetate (3x). The organics were washed with water and dried (saturated NaCl, MgSO₄). This was concentrated to a solid which was triturated with ethyl ether to give an off-white powder. This solid was combined with another lot (3.06 g total) and the hemi-fumarate was formed in isopropanol to give 3.14 g of a white powder. This was twice recrystallized from methanol/ethyl ether to give 2.25 g of a white powder, m.p. 190°–193° C. (dec.).

ANALYSIS: Calculated for $C_{15}H_{17}N_3O\cdot\frac{1}{2}C_4H_4O_4\cdot H_2O$: 61.61%C, 6.39%H, 12.68%N. Found: 61.17%C, 6.13%H, 12.53%N.

EXAMPLE 14

1-Azido-1,2,3,4-tetrahydro-9-acridinamine, maleate

A mixture of 9-amino-1,2,3,4-tetrahydroacridin-1-ol (17.2 g), triphenylphosphine (23.2 g), diethyl azodicarboxylate (13.9 ml) and diphenylphosphorylazide (19.0 ml) in 500 ml of tetrahydrofuran was heated at 65° C. for 65 hours. The solution was then concentrated off and the desired acid was purified via flash chrometography (EtOAC→2% Et₃N/EtOAC) to give 9.48 g of a yellow solid, m.p. 124°–126° C. (dec.).

A 3.13 g portion of the free base was dissolved in isopropanol and 1 equivalent of maleic acid was added. The resulting solid was collected and twice recrystallized from methanol/ethyl ether to give 1.75 g of a yellow powder, m.p. 163°–165° C. (dec.).

ANALYSIS: Calculated for $C_{13}H_{13}N_5\cdot C_4H_4O_4$: 57.46%C, 4.82%H, 19.71%N. Found: 57.84%C, 4.84%H, 19.27%N.

EXAMPLE 15

1,2,3,4-Tetrahydro-1,9-acridinediamine, dimaleate

To a suspension of 10% palladium on charcoal (314 mg) in 200° ethanol charged in a Parr pressure vessel was added a solution of 1-azido-1,2,3,4-tetrahydro-9- acridinamine (4.7 g) in 125 ml of ethanol. This was pressurized to 50 psi with hydrogen and shaken for 2.5 hours.

The catalyst was filtered and the desired amino compound was purified via flash chromatography (EtOAC/Et₃N/MeOH; 90:5:5) to give 2.72 g of an off-white powder, m.p. 167°–171° C. This was dissolved in isopropanol and treated with 2 equivalents of maleic acid in isopropanol. The dimaleate was collected and recrystallized from methanol/ethyl ether to give 4.27 g of a white powder, m.p. 187°–190° C. (dec.).

ANALYSIS: Calculated for $C_{13}H_{15}N_3.2.0C_4H_4O_4$: 56.63%C, 5.20%H, 9.43%N. Found: 56.40%C, 5.07%H, 9.32%N.

EXAMPLE 16

N₁-Ethyl-1,2,3,4-tetrahydrol, 9-acridinediamine, fumarate, hemi-hydrate

2-Methyl-3a,4,5,6-tetrahydro-(3H)-pyrimidino[4,5,6-k,l]acridine (4.5 g) was suspended in 100 ml of tetrahydrofuran and treated with 39 ml of a 1 molar lithium aluminum hydride solution in tetrahydrofuran. This was refluxed overnight.

The reaction was quenched with a saturated NH₄Cl solution, the resulting precipitate filtered away and the filtrate was dried (MgSO₄).

The desired compound was purified via flash chromatography (2.5% Et₃N/EtOAc) to give 2.9 g of a yellow powder. This was dissolved in isopropanol and treated with solid fumaric acid to give 3.75 g of a white solid. This was twice recrystallized from methanol/ethyl ether to give 2.68 g of a white powder m.p. 164°–167° (dec.).

ANALYSIS: Calculated for $C_{15}H_{19}N_3.C_4H_4O_4.0.5-H_2O$: 62.28%C, 6.33%H, 11.47%N. Found: 62.35%C, 6.27%H, 11.40%N.

We claim:

1. A compound of the formula

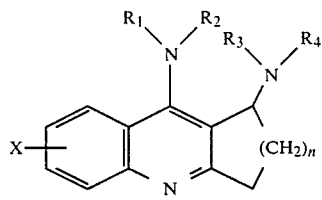

where
n is 1, 2 or 3;
X is hydrogen, loweralkyl, loweralkoxy, halogen, hydroxy, nitro or trifluoromethyl;
R₁ and R₂ are each independently hydrogen, loweralkyl or arylloweralkyl, but both may not be arylloweralkyl simultaneously;
R₃ and R₄ are each independently hydrogen, loweralkyl, arylloweralkyl, formyl or loweralkylcarbonyl, or alternatively the group —NR₃R₄ taken as a whole constitutes

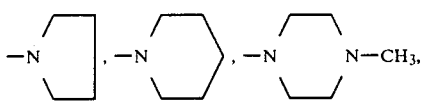

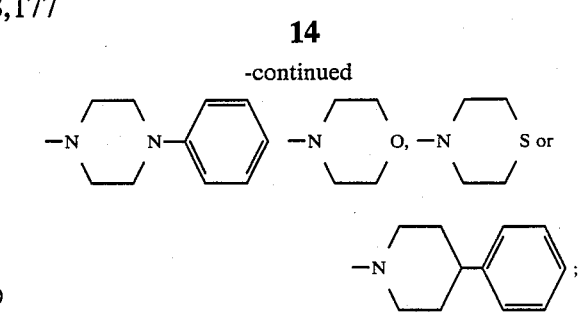

a stereo isomer thereof or a pharmaceutically acceptable acid addition salt thereof.

2. The compound as defined in claim 1, where n is 2.
3. The compound as defined in claim 2, where X is hydrogen.
4. The compound as defined in claim 3, where R₁ is hydrogen.
5. The compound as defined in claim 4, where R₂ is hydrogen.
6. The compound as defined in claim 2, where the group —NR₃R₄ taken as a whole is

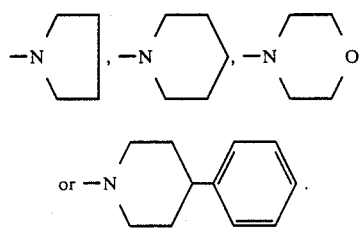

7. The compound as defined in claim 3, where the group —NR₃R₄ taken as a whole is

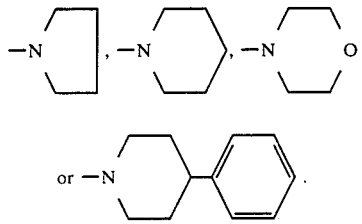

8. The compound as defined in claim 4, where the group —NR₃R₄ taken as a whole is

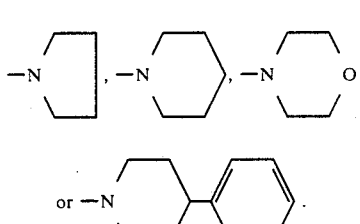

9. The compound as defined in claim 5, where the group —NR₃R₄ taken as a whole is

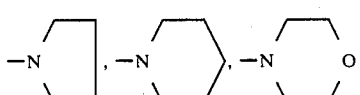

or 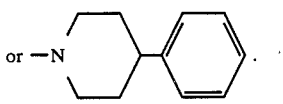

10. The compound as defined in claim 1, which is 1-(1-pyrrolidinyl)-1,2,3,4-tetrahydro-9-acridinamine.

11. The compound as defined in claim 1, which is 1-(1-piperidinyl)-1,2,3,4-tetrahydro-9-acridinamine.

12. The compound as defined in claim 1, which is 1-(4-morpholinyl)-1,2,3,4-tetrahydro-9-acridinamine.

13. The compound as defined in claim 1, which is 1-(4-phenyl-1-piperidinyl)-1,2,3,4-tetrahydro-9-acridinamine.

14. The compound as defined in claim 1, which is $N_1$-propyl-1,2,3,4-tetrahydro-1,9-acridinediamine.

15. The compound as defined in claim 1, which is $N_1$-butyl-1,2,3,4-tetrahydro-1,9-acridinediamine.

16. The compound as defined in claim 1, which is $N_1$-benzyl-1,2,3,4-tetrahydro-1,9-acridinediamine.

17. The compound as defined in claim 1, which is $N_1$-(3,4-dimethoxybenzyl)-1,2,3,4-tetrahydro-1,9-acridinediamine.

18. The compound as defined in claim 1, which is $N_1$-(2-phenylethyl)-1,2,3,4-tetrahydro-1,9-acridinediamine.

19. The compound as defined in claim 1, which is 1-(4-methyl-1-piperazinyl)-1,2,3,4-tetrahydro-9-acridinamine.

20. The compound as defined in claim 1, which is 1-(4-phenyl-1-piperazinyl)-1,2,3,4-tetrahydro-9-acridinamine.

21. The compound as defined in claim 1, which is $N_1$-hexanoxyl-1,2,3,4-tetrahydro-1,9-acridinediamine.

22. The compound as defined in claim 1, which is $N_1$-acetyl-1,2,3,4-tetrahydro-1,9-acridinediamine.

23. The compound as defined in claim 1, which is 1,2,3,4-tetrahydro-1,9-acridinediamine.

24. The compound as defined in claim 1, which is $N_1$-ethyl-1,2,3,4-tetrahydro-1,9-acridinediamine.

25. A pharmaceutical composition comprising an effective memory enhancing amount of a compound as defined in claim 1 and a suitable carrier therefor.

26. A method of treating a memory dysfunction characterized by decreased cholinergic function, which comprises administering to a patient in need of relief from such memory dysfunction an effective amount of a compound as defined in claim 1.

* * * * *

UNITED STATES PATENT AND TRADEMARK OFFICE
CERTIFICATE OF CORRECTION

PATENT NO.   :   4,868,177

DATED        :   September 19, 1989

INVENTOR(S)  :   Gregory Michael Shutske and Kevin James Kapples

It is certified that error appears in the above-identified patent and that said Letters Patent is hereby corrected as shown below:

On the title page:

The Filing Date should read "November 9, 1988" instead of "November 29, 1988".

Signed and Sealed this

Twenty-second Day of May, 1990

Attest:

HARRY F. MANBECK, JR.

*Attesting Officer*  *Commissioner of Patents and Trademarks*